United States Patent
Wieland et al.

(10) Patent No.: US 11,076,897 B2
(45) Date of Patent: *Aug. 3, 2021

(54) ORTHOPEDIC LOCKING SCREW FOR AN ORTHOPEDIC FASTENING SYSTEM

(71) Applicant: Stryker European Holdings I, LLC, Kalamazoo, MI (US)

(72) Inventors: Manfred Wieland, Kiel (DE); Nils Zander, Eckernförde (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 217 days.

This patent is subject to a terminal disclaimer.

(21) Appl. No.: 15/776,667

(22) PCT Filed: Nov. 18, 2015

(86) PCT No.: PCT/US2015/061333
§ 371 (c)(1),
(2) Date: May 16, 2018

(87) PCT Pub. No.: WO2017/086953
PCT Pub. Date: May 26, 2017

(65) Prior Publication Data
US 2018/0368894 A1  Dec. 27, 2018

(51) Int. Cl.
*A61B 17/72* (2006.01)
*A61B 17/80* (2006.01)
(Continued)

(52) U.S. Cl.
CPC ........ *A61B 17/725* (2013.01); *A61B 17/8042* (2013.01); *A61B 17/863* (2013.01);
(Continued)

(58) Field of Classification Search
CPC . A61B 17/725; A61B 17/8057; A61B 17/863; A61B 17/866; A61B 17/8042;
(Continued)

(56) References Cited

U.S. PATENT DOCUMENTS 3,731,724 A    5/1973  Dorflinger
5,259,398 A *  11/1993  Vrespa ................. A61B 17/863
                                                      128/898

(Continued)

FOREIGN PATENT DOCUMENTS

DE    20307265 U1   7/2003
EP     2228015 A3   3/2011
(Continued)

OTHER PUBLICATIONS

International Search Report for Application No. PCT/US2015/061333 dated Jun. 27, 2016.
(Continued)

*Primary Examiner* — Kevin T Truong
*Assistant Examiner* — Marcela I. Shirsat
(74) *Attorney, Agent, or Firm* — Lerner, David, Littenberg, Krumholz & Mentlik, LLP

(57) ABSTRACT

An orthopedic locking screw is configured to be retained inside a bore of an orthopedic implant. The orthopedic locking screw includes a shaft extending axially, a casing secured around an outer surface of the shaft, a deformable thread disposed along an outer surface of the casing, and a forward external thread disposed on the shaft. The forward external thread has a pitch that is different from a pitch of the deformable thread of the casing. Further, an orthopedic locking screw is provided, wherein projections and the casing are alternately arranged on the outer surface of the shaft.

20 Claims, 6 Drawing Sheets

(51) Int. Cl.
*A61B 17/86* (2006.01)
*A61B 17/68* (2006.01)

(52) U.S. Cl.
CPC ........ *A61B 17/866* (2013.01); *A61B 17/8635* (2013.01); *A61B 17/8685* (2013.01); *A61B 17/686* (2013.01); *A61B 2017/8655* (2013.01)

(58) Field of Classification Search
CPC ........ A61B 17/8685; A61B 2017/8655; A61B 17/8635; A61B 17/686
USPC ................ 606/312, 315–316, 327
See application file for complete search history.

(56) References Cited

U.S. PATENT DOCUMENTS

| | | | |
|---|---|---|---|
| 5,454,813 | A | 10/1995 | Lawes |
| 6,030,162 | A | 2/2000 | Huebner |
| 6,129,730 | A | 10/2000 | Bono et al. |
| 6,355,043 | B1 | 3/2002 | Adam |
| 7,935,138 | B1 | 5/2011 | Richelsoph |
| 8,162,998 | B2 | 4/2012 | Schlienger et al. |
| 8,241,287 | B2 | 8/2012 | Prager et al. |
| 2001/0049528 | A1 | 12/2001 | Kubota |
| 2006/0064095 | A1 | 3/2006 | Senn et al. |
| 2006/0095040 | A1* | 5/2006 | Schlienger ........... A61B 17/686 606/64 |
| 2006/0149247 | A1 | 7/2006 | Frigg et al. |
| 2008/0255558 | A1 | 10/2008 | Schlienger et al. |
| 2009/0171396 | A1 | 7/2009 | Baynham et al. |
| 2009/0248089 | A1* | 10/2009 | Jacofsky ............. A61B 17/686 606/311 |
| 2010/0179550 | A1 | 7/2010 | Schreiber et al. |
| 2010/0228301 | A1* | 9/2010 | Greenhalgh ......... A61B 17/686 606/313 |

FOREIGN PATENT DOCUMENTS

| | | |
|---|---|---|
| WO | 2012107056 A1 | 8/2012 |
| WO | 2013075730 A1 | 5/2013 |
| WO | WO-2015172842 A1 * | 11/2015 ........... A61B 17/861 |

OTHER PUBLICATIONS

International Search Report for Application No. PCT/EP2014/060089 dated Aug. 18, 2014.

* cited by examiner

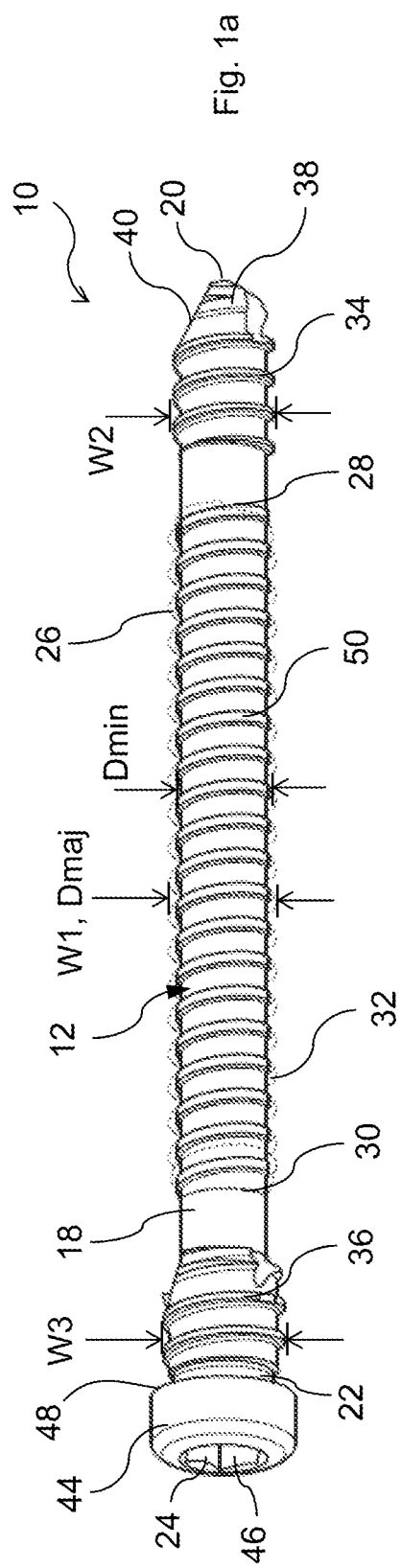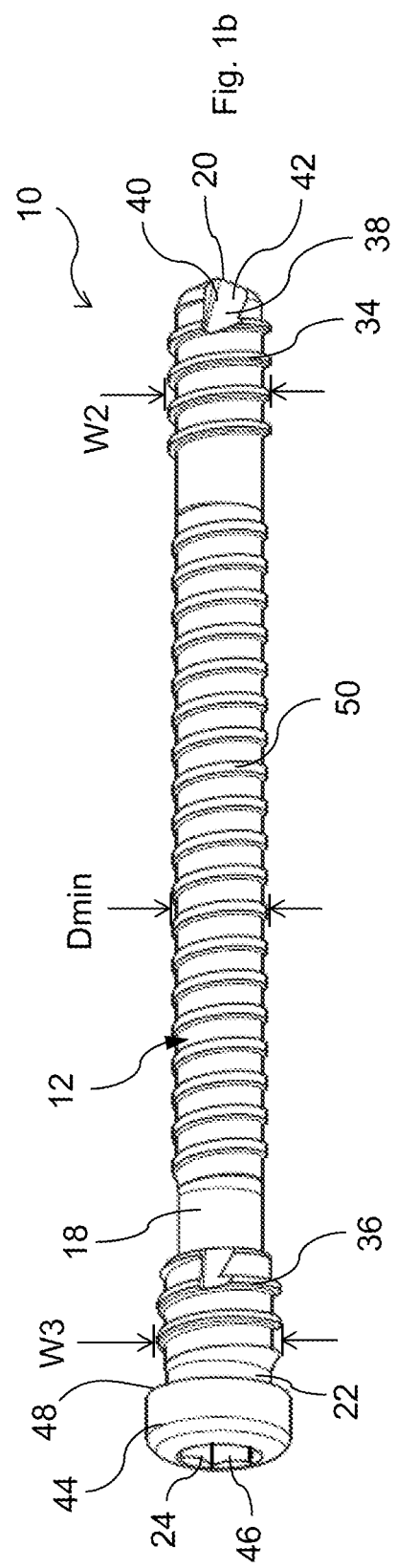

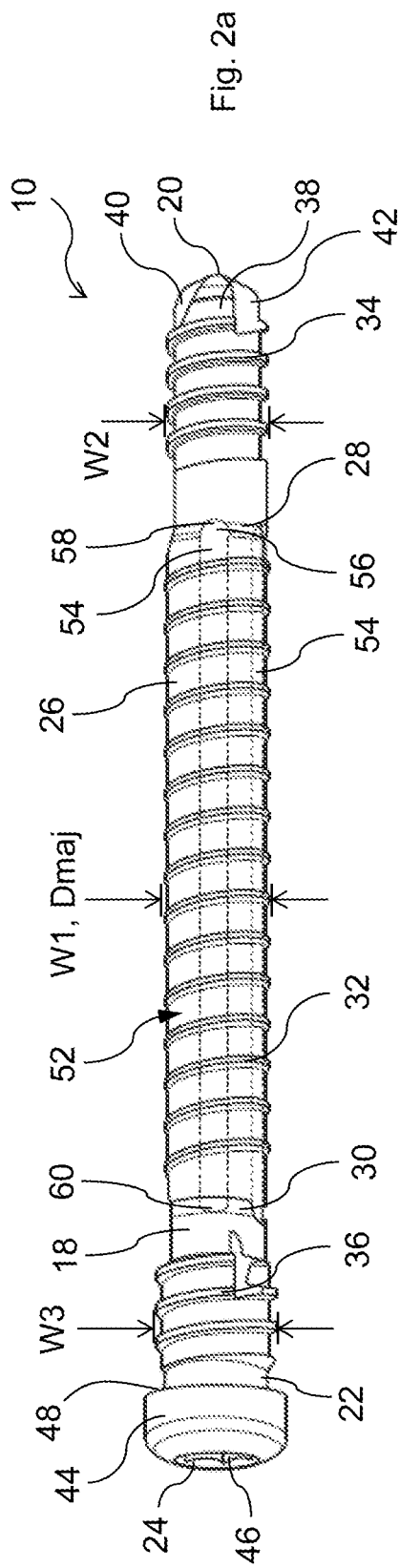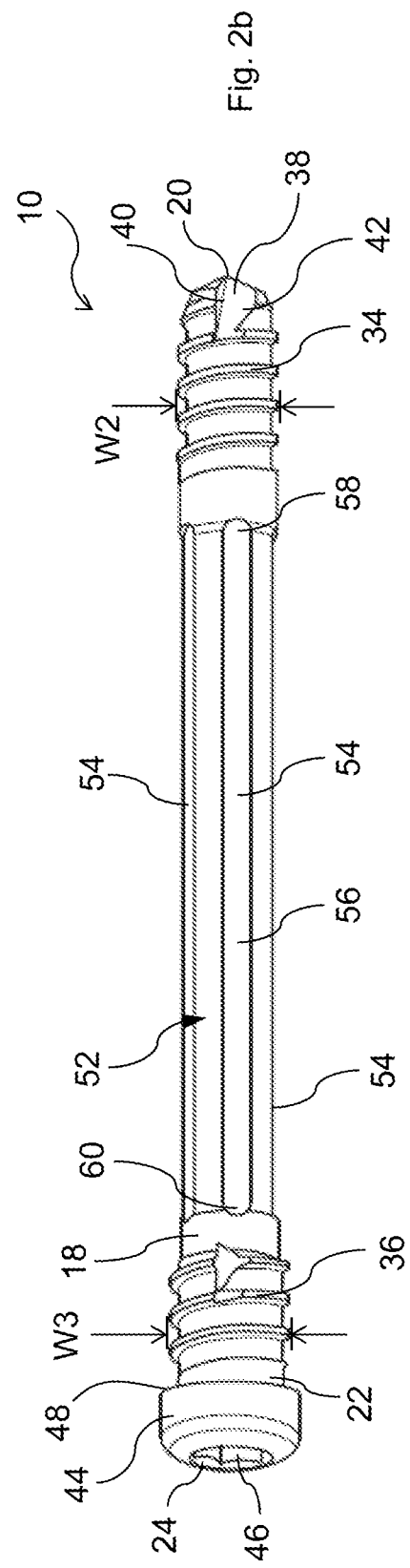

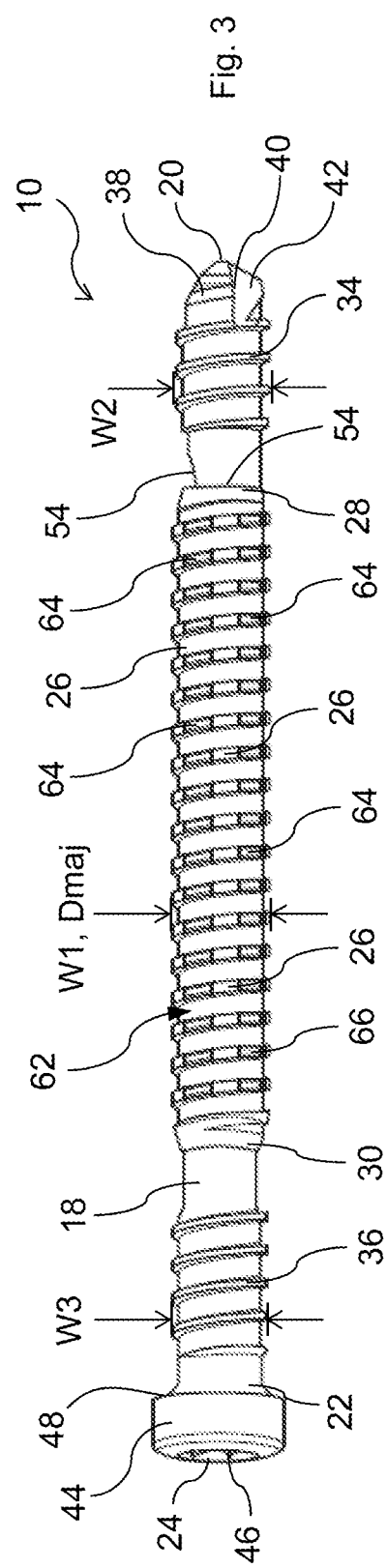

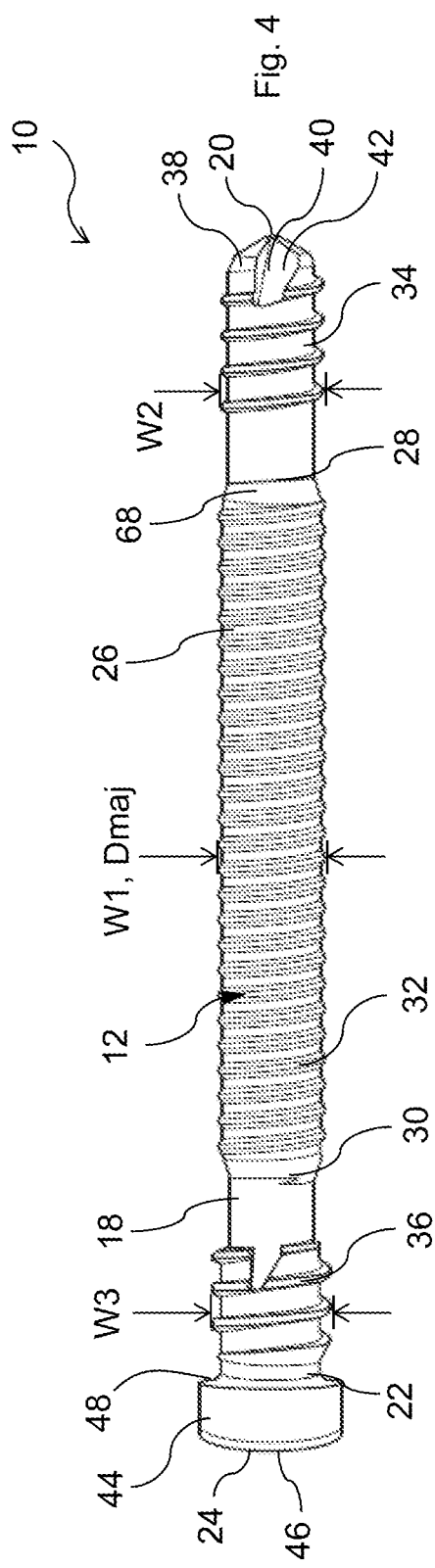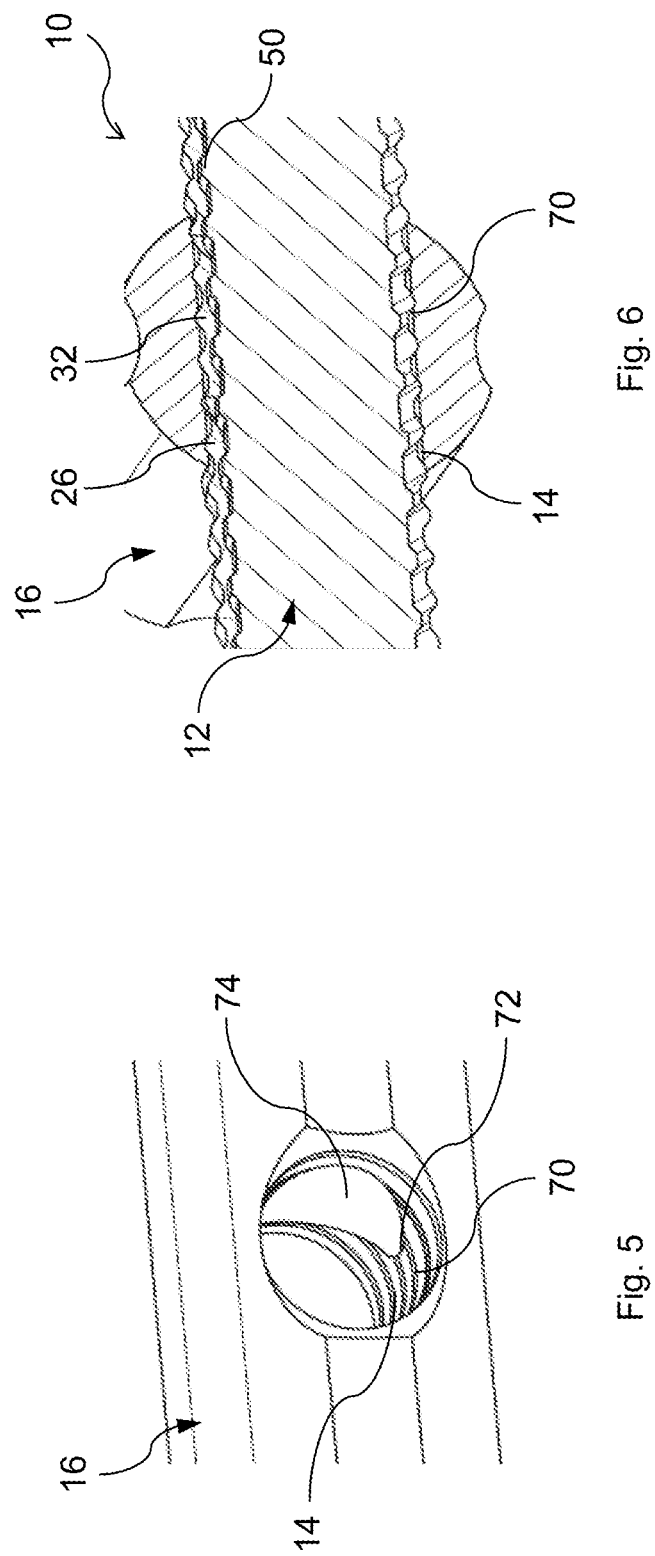

ORTHOPEDIC LOCKING SCREW FOR AN ORTHOPEDIC FASTENING SYSTEM

CROSS-REFERENCE TO RELATED APPLICATIONS

The present application is a national phase entry under 35 U.S.C. § 371 of International Application No. PCT/US2015/061333 filed Nov. 18, 2015, published in English, the disclosure of which is incorporated herein by reference.

BACKGROUND OF THE INVENTION

The present disclosure relates to orthopedic locking screws, orthopedic fastening systems including such orthopedic locking screws, and methods of securing an orthopedic locking screw in a bore of an orthopedic implant.

In orthopedic procedures, it is often necessary to secure an orthopedic implant. In such cases, an orthopedic fastening system may be provided in which an orthopedic locking screw is used to secure an orthopedic implant to a bone or to another orthopedic implant.

One exemplary arrangement of such an orthopedic fastening system comprises an intramedullary bone nail to secure two or more bone pieces together. One or more orthopedic locking screws are used to secure the bone pieces to the intramedullary bone nail. One exemplary arrangement of an intramedullary bone nail secured to bone pieces with locking screws is shown in WO 2013/075730 A1.

Another bone screw disclosed in U.S. Pat. No. 8,162,998 includes a radially expandable sleeve with internal threads that is threaded onto a threaded end of the screw. Further, EP 2 228 015 A2 discloses an expandable locking screw having an outer shell that fits over and covers the distal end of a shaft. The outer shell has outer threads and a tip designed for seating into bone. A locking screw disclosed in U.S. Pat. Pub. No. 2010/0179550 A1 slides into and through a sleeve, wherein a clamping screw presses against the sleeve to lock the screw and the sleeve to the shaft of an intramedullary nail. U.S. Pat. No. 5,454,813 discloses a sleeve that slides onto a lag screw and completely prevents rotation of the screw inside the bore of an intramedullary nail. Further technological background can be found in U.S. Pat. Pub. No. 2006/0149247 A1.

Often there is a small radial gap or interval between the outer diameter of the locking screw and the inner diameter of the bore of the orthopedic implant that operably receives the locking screw. The resulting radial play can allow shifting and movement of the bone and/or locking screw relative to the orthopedic implant and/or relative to other bone portions secured by the orthopedic implant. Such shifting and movement may slow down or otherwise have a negative effect on healing of the fracture.

In order to eliminate or minimize this play between the connected parts, it is common to use additional screws or components. This, however, increases the number of parts used and inserted into the body and may increase the necessary healing time.

BRIEF SUMMARY OF THE INVENTION

There is a need for an orthopedic locking screw configured to be used as part of an orthopedic fastening system that, in at least some cases, may reduce or eliminate the amount of shifting and movement between parts of the orthopedic fastening system and/or reduce the number of additional components needed to sufficiently minimize any such movement.

According to some aspects of the present disclosure, an orthopedic locking screw configured to be secured through a bore of an orthopedic implant comprises a shaft extending axially between a first end and a second end. A casing is secured to and rotationally fixed around an outer surface of the shaft. The casing has a first end proximate the first end of the shaft and a second end proximate the second end of the shaft. A deformable thread is disposed along an outer surface of the casing. A forward external thread is disposed on the shaft between the first end of the casing and the first end of the shaft. The forward external thread has a pitch that is different from a pitch of the deformable thread of the casing.

According to some aspects, an orthopedic fastening system includes an orthopedic implant comprising a bore and an orthopedic locking screw configured to be retrained inside the bore. The orthopedic locking screw comprises a shaft extending axially between a first end and a second end, the first end sized to be received in the bore; a casing secured to and rotationally fixed around an outer surface of the shaft, the casing having a first end proximate the first end of the shaft and a second end proximate the second end of the shaft; a deformable thread disposed along an outer surface of the casing, wherein the deformable thread is configured to engage a substantially complementary internal thread feature of the bore; and a forward external thread disposed on the shaft between the first end of the casing and the first end of the shaft, wherein the forward external thread has a pitch that is different from a pitch of the deformable thread of the casing. In other arrangements, the orthopedic locking screw may include any one of the embodiments and variations shown and/or described herein, and the orthopedic implant may be any type of orthopedic implant with a bore.

According to some aspects, an orthopedic locking screw configured to be secured through a bore of an orthopedic implant comprises a shaft having projections disposed on an outer surface of the shaft and a casing secured to and rotationally fixed around the outer surface of the shaft, wherein the casing is formed of a deformable material. The projections and the casing are alternately arranged on the outer surface of the shaft, such that the projections and the casing together form a thread-like feature along the shaft.

According to some aspects, a method of securing an orthopedic screw in a bore of an orthopedic implant is provided. The method comprises the step of providing an orthopedic locking screw including a shaft extending axially between a first end and a second end, the first end sized to be received in the bore; a drive member disposed at the second end; a casing secured to and rotationally fixed around an outer surface of the shaft, the casing having a first end proximate the first end of the shaft and a second end proximate the second end of the shaft; a deformable thread disposed along an outer surface of the casing; and a forward external thread disposed on the shaft between the first end of the casing and the first end of the shaft, wherein the forward external thread has a pitch that is different from a pitch of the deformable thread of the casing. The method further includes the steps of inserting the first end of the shaft into the bore; engaging the deformable thread of the casing with the bore; rotating the drive member to rotate the shaft and the casing so as to operably (e.g., threadably) engage the deformable thread with the orthopedic implant, thereby achieving an advance of the orthopedic locking screw through the bore; engaging the forward external thread with bone on a opposite side of the orthopedic implant; rotating the drive member further to rotate the shaft and the casing so as to operably (e.g., threadably) engage the forward external thread with bone, wherein, upon the operable engagement of the forward external thread with bone, the different thread pitches result in a (e.g., further) deformation of the deformable thread of the casing against the orthopedic implant.

According to some aspects, a method of securing an orthopedic screw in a bore of an orthopedic implant is provided, wherein the method comprises the steps of drilling a bore having a first diameter into bone; widening at least a part of the bore by drilling with a second diameter; and providing an orthopedic locking screw. The orthopedic locking screw includes a shaft extending axially between a first end and a second end; a drive member disposed at the second end; a casing secured to and rotationally fixed around an outer surface of the shaft, wherein the casing is formed of a deformable material, wherein the casing has an outer cross-sectional width that is larger than a smallest inside cross-sectional width of the bore of the orthopedic implant and the first end of the shaft has an outer cross-sectional width that is smaller than the smallest inside cross-sectional width of the bore of the orthopedic implant but larger than the first diameter of the bore in the bone. The method further includes the steps of inserting the first end of the shaft into the bore of the orthopedic implant; engaging the casing with the bore of the orthopedic implant; rotating the drive member to rotate the shaft and the casing so as to operably (e.g., threadably) engage the casing with the orthopedic implant, thereby achieving an advance of the orthopedic locking screw through the bore of the orthopedic implant; engaging the first end of the shaft with the bore having the first diameter in the bone on an opposite side of the orthopedic implant; rotating the drive member further to rotate the shaft and the casing so as to operably (e.g., threadably) engage the first end of the shaft with bone, wherein, upon the operable engagement of the first end of the shaft with bone, the further rotation results in a (e.g., further) deformation of the casing against the orthopedic implant.

In other forms of the methods described above, the orthopedic screw may include any one of the embodiments and variations shown and/or described herein, and the orthopedic implant may include any orthopedic implant with a bore, such as described and/or shown herein.

Any one of these aspects may optionally include any one or more of the following arrangements and/or features in any operably compatible combination and form.

In some arrangements, for example, the orthopedic locking screw may be realized in the form of a threaded or unthreaded bolt.

In some arrangements, the orthopedic implant is, for example, an intramedullary bone nail, with one or more bores extending partially or completely therethrough for receiving a locking screw therein. The orthopedic implant is not limited to an intramedullary bone nail. The orthopedic implant may be, for example, a plate or bone connector, or another type of orthopedic implant.

In some arrangements, the bore of the orthopedic implant optionally defines an internal surface feature, such as an internal thread feature, including one or more internally projecting ribs, tabs, lips or threads that are configured to engage with the casing (e.g., with external engagement features like the deformable thread thereof) to retain and/or advance the screw into and/or through the bore. The internal surface features may define a helical path or may not define a helical path. The bore may be an internally threaded bore. The bore may be a through bore or a blind bore.

The casing may be integrally formed with the deformable thread. The casing and/or the deformable thread may be formed from material that is at least partially plastically deformable. Additionally, or in the alternative, the casing and/or the deformable thread may be formed of a material that is at least partially elastically deformable.

In any of the aspects, in particular the method aspects, presented herein, an optional threadable engagement of the orthopedic screw with bone may pull the shaft and the casing through the bore and achieve the deformation of the deformable thread of the casing against the orthopedic implant. As such, this threadable engagement with bone may achieve a different (e.g., faster or slower) advance of the orthopedic locking screw through bone than previously through to the bore of the orthopedic implant.

In one implementation, the casing is configured to develop a press-fit pressure against an opposing surface feature of the orthopedic implant (e.g., the bore thereof), such as an inside surface, edge, and/or an inside thread feature. Generally, the casing may be formed from a material that is more deformable (i.e., softer) than the screw shaft. The casing may be formed of a rubbery (e.g., polymeric) material, such as rubber or silicon or other polymer like poly-L-lactide acid (PLLA). The material of the casing may have a lesser hardness than the opposing inner surface and/or surface features of the bore of the orthopedic implant. The casing may be formed, for example, of a polymer or a metal capable of plastic deformation upon engaging the bore. The press-fit pressure may be semi-resilient such that the press-fit pressure is operable to lockingly grip or otherwise retain the screw in the bore. In some instances, this may provide an angularly stable connection between the orthopedic locking screw and the bore of the orthopedic implant.

In some arrangements, one or more of the each of the shaft, the casing, and the orthopedic implant is formed of a bio-compatible material suitable and/or approved for use as an implant in a human and/or animal. The material of the casing may be softer than the material of at least one of the shaft and the internal surface feature and/or surface of the bore of the orthopedic implant. The material of the casing may include at least one of a plastic, polymer and a metal. The material of one or both of the shaft and the orthopedic implant may include at least one of a plastic, polymer, a metal, and a ceramic.

In some arrangements, the external surface of the casing is substantially smooth and/or includes substantially smooth areas, which do not include any engagement features. In one realization, one or more engagement features are disposed on the outer surface of the casing. An individual engagement feature is configured to operably engage with the bore of the implant, for example, to operably engage one or more internal surface features in the bore, such as one or more internal threads, tabs, ridges, lips and/or edges on the bore, in such a manner so as to retain and/or advance the shaft in the bore with a mechanical interfit. The engagement feature may include a protrusion or a recess that interacts with a thread feature of the bore, for example, in a manner similar to threaded engagement, although the engagement feature need not necessarily be a helical thread. For example, the engagement feature may include projections, such as tabs or ridges. The engagement feature may include recesses, such as grooves. The engagement features may define a helical path or may not define a helical path. The engagement features may be configured to engage the surface features of the bore to retain and/or to advance the shaft in the bore with a mechanical interfit between complementary engagement features on the casing and the bore, such as a mechanical interfit between threads or thread-like features. The engagement feature may be deformable or rigid. The engagement feature may be formed of the same material as the casing, such as by molding or machining the outer surface of the casing. The engagement feature may be formed of a different material than the casing and secured to the outer surface of the casing, such as by molding into the casing material, welding, for example with heat and/or chemicals, and/or adhering, for example with adhesive.

In some arrangements, the engagement feature may include an external thread. The external thread may be a continuous thread or an intermittent thread. The external thread may be a deformable thread. The deformable thread may be configured to engage an internal thread feature of the bore. Thus, the deformable thread of the casing can be a continuous thread extending from adjacent the first end of the casing to the second end of the casing. The deformable thread may be molded or machined into the outer surface of the casing. The deformable thread may be formed of the same material as the rest of the casing.

In one implementation, the deformable thread of the casing may define a pitch. The pitch of the deformable thread may be constant along the length of the deformable thread (i.e., along the direction of the axis thereof). In some arrangements, the deformable thread may have a variable pitch that varies along the direction of the axis. The pitch may vary from a smaller pitch proximate the first end of the shaft to a larger pitch proximate the second end of the shaft. The pitch may vary continuously or the pitch may vary discontinuously. In these arrangements, when the casing is operably threadedly engaged with the bore of the implant, an axial press-fit pressure is formed between the bore and the axial sides of the deformable threads, thereby helping to form a press-fit locking action between the casing and the bore. The deformable thread can be configured to operably engage with the bore so as to retain the shaft in the bore of the implant, for example with a press-fit and/or a mechanical interfit. In one implementation, the pitch of the deformable thread of the casing can be substantially equal to the pitch of the internal thread feature of the bore of the orthopedic implant. Alternatively, the pitch of the deformable thread of the casing can be slightly different from the pitch of the internal thread feature of the bore of the orthopedic implant. The pitch of the deformable thread of the casing may also be larger or smaller than the pitch of the internal thread feature of the bore of the orthopedic implant.

In one realization, the forward external thread may define a pitch. The pitch of the forward external thread may be constant along the direction of the axis thereof. In one implementation, the pitch of the forward external thread can be larger than the pitch of the deformable thread of the casing. Alternatively, the pitch of the forward external thread may be smaller than the pitch of the deformable thread of the casing. The pitch of the forward external thread may be substantially equal to the pitch of the deformable thread of the casing.

In some implementations, the orthopedic locking screw may include a rear external thread. The rear external thread can be disposed on the shaft between the second end of the shaft and the second end of the casing. The rear external thread may have a pitch. The pitch of the rear external thread can be constant along the direction of the axis thereof. In one realization, the pitch of the rear external thread may be equal to the pitch of the forward external thread. Alternatively, the pitch of the rear external thread may be larger or smaller than the pitch of the forward external thread. Further, at least one of the forward external thread and the rear external thread may be axially spaced apart from the casing. The forward and rear external threads may be spaced apart from each other axially along the shaft. The forward external thread may be spaced axially from the first end of the casing or may extend completely to the first end of the casing. The rear external thread may be spaced axially from the second end of the casing or may extend completely to the second of the casing. Portions of one or both of the forward and rear external threads may extend underneath the respective ends of the casing. Alternatively, the forward and rear external threads may be connected with each other, for example, underneath the casing.

In some arrangements, the deformable thread may have a minor diameter and a major diameter. At least one of the minor and major diameters can be constant along the length of the deformable thread. The minor diameter or the major diameter (i.e., the outer diameter) of the deformable thread can be larger than the largest outside diameter of the first end of the shaft and/or any threads (e.g., the forward external thread) formed on the first end of the shaft. In one implementation, the casing can have an outer cross-sectional width that is larger than a cross-sectional width of the first end if the shaft adjacent the first end of the casing.

The deformable thread may have a variable depth, such as with a minor diameter and/or with a major diameter that increases continuously or discontinuously in the direction from the first end of the casing toward the second end of the casing. The deformable thread may extend continuously or intermittently along the casing. The deformable thread may extend from adjacent the first end of the casing. The deformable thread may have a second end at the second end of the casing or spaced axially from the second end of the casing. Where the first end of the casing is tapered, the deformable thread may have a first end along the tapered portion. The first end of the deformable thread may be spaced from the first end of the casing.

The minor diameter of the deformable thread may be larger than a corresponding smallest opening width of the bore of the orthopedic implant, such as the minor diameter of any internal thread features of the bore. In some arrangements, a major diameter of the deformable thread can be larger than a major diameter of an internal thread of the bore. In these arrangements, when the casing is operably engaged with the bore, such as by threaded engagement, a radial press-fit pressure is formed between the bore and an outer radial surface of the casing, thereby helping to form a press-fit locking action between the casing and the bore.

In one realization, the diameter of the deformable thread of the casing may be substantially equal to the diameter of the internal thread feature of the bore of the orthopedic implant. The deformable thread may be substantially equal to the internal thread of the bore of the orthopedic implant. Thus, the diameter and pitch of the deformable thread may be equal to the diameter and the pitch of the internal thread of the bore of the orthopedic implant.

In some implementations, a minor diameter of the external thread on the casing is larger than the largest outside diameter of the first end of the shaft. If a thread is disposed on the first end of the shaft, the minor diameter of the deformable thread may be larger than a major diameter or outside cross-sectional measurement of the thread. The outer diameter of the deformable thread of the casing can thus be larger than the outer diameter of the forward external thread. Further, the inside diameter of the bore of the orthopedic implant can be larger than the outer diameter of the forward external thread. Thus, the forward external thread may have a major diameter that is smaller than the smallest inside diameter of any internal thread feature of the bore, such as the minor diameter of an internal thread. The outer diameter of the rear external thread may be larger than the outer diameter of the deformable thread of the casing. Alternatively or in addition, the outer diameter of the rear external thread can be equal to or larger than the outer diameter of the forward external thread.

In some arrangements, the outer surface of the first end of the casing is tapered radially inwardly toward the outer surface of the shaft. The first end of the casing may be tapered to the same radius or other outer cross-sectional dimension of the adjacent portion of the first end of the shaft so as to have a smooth transition between the outer surface of the first end of the shaft and the outer surface of the first end of the casing. Alternatively, the first end of the casing may have a larger radius or other outer cross-sectional dimension than the adjacent portion of the first end of the shaft so as to form a radially stepped transition between the outer surface of the first end of the shaft and the outer surface of the first end of the casing. The outer surface of the casing may be tubular with a constant cross-sectional dimension, such as being cylindrical, along the entire length thereof or along some less than entire portion thereof.

The casing may be secured to the outer surface of the shaft in any manner sufficient to prevent rotational and/or axial sliding of the casing relative to the shaft, for example, when the casing is rotationally engaged against an outer or internal surface of the bore. The casing may be molded directly against the outer surface of the shaft so as to provide a molded securement between the casing and the outer surface of the shaft. The casing may be adhesively secured to the outer surface of the shaft with an adhesive. The casing may be mechanically secured to the outer surface of the shaft, for example, by engagement with projections or other surface features with the shaft, such as threads, ribs, tabs, grooves, and/or scoring. The shaft may have a polygonal or other non-circular profile (i.e., cross-sectional shape transverse to the longitudinal axis of the shaft) that prevents the casing from rotating relative to the shaft.

In some arrangements, the shaft includes at least one groove. The groove may receive some or all of the casing. The inner radial surface of the casing may be secured against the surface of the groove, such as by mechanical interaction, molding, welding, and/or with adhesive.

The groove may extend circumferentially around the shaft (e.g., in the form of a radial groove or thread). Additionally, or as an alternative, the groove may extend axially along the shaft. The groove may have a generally polygonal core profile. The groove may have a generally arcuate core profile, such as circular or oval. Further, the groove may include both arcuate core profiles and polygonal core profiles. The groove may include one or both of a first shoulder proximate the first end of the shaft and a second shoulder proximate the second end of the shaft. The first and/or second shoulders may at least partially secure the casing axially and/or radially on the shaft. The first end of the casing may engage the first shoulder and/or the second end of the casing may engage the second shoulder. The casing may have a thickness larger than a radial depth of the groove such that the outer diameter or other outside cross-sectional dimension of the casing is larger than an outer diameter or other outside cross-sectional dimension of the first end of the shaft adjacent the casing.

The casing and/or the shaft may have different cross-sectional shapes, as measured radially and orthogonally to the axis of the shaft, for example. The casing and/or the shaft may be substantially cylindrical, with a substantially circular cross-section, as measured orthogonally to the axis of the shaft, for example. However, the cross-section does not necessarily have to be circular, and may be partially or totally elliptical or have other arcuate shapes. The shaft may have an elongate polygonal profile, such as a rectangular, square, hexagonal, or other polygonal shape or have longitudinal ribs or grooves or other protrusions or recesses.

In some arrangements, the outer cross-sectional width of the casing corresponds to an outside diameter of the casing. If the casing includes a thread feature, such as an external thread feature, the outer cross-sectional width of the casing may be an inner diameter of the thread feature or an outer diameter of the thread feature.

In some arrangements, the cross-sectional width of the shaft is an outside diameter of the shaft. The cross-sectional width of the shaft may be immediately adjacent the first end of the casing. If a thread feature is disposed at the first end of the shaft, the cross-sectional width of the shaft may be an inner diameter of the thread feature or an outer diameter of the thread feature.

The orthopedic locking screw may further include a drive member. The drive member may be disposed at the second end of the shaft. In some arrangements, the drive member includes a head configured to engage with a rotational drive member, such as a screw driver or wrench. The head may have a larger, the same, or a smaller cross-sectional width than the second end of the shaft adjacent the head. The head may form a shoulder that extends radially outwardly from an outer surface of the shaft to an outer surface of the head. For example, the head may have an outside diameter that is larger than the outside diameter of the adjacent portion of the second end of the shaft. However, the head may have a circular cross-sectional shape or a non-circular cross-sectional shape, such as partially or totally elliptical and/or polygonal.

In some arrangements, the first end of the shaft includes a tip, optionally having a self-tapping feature. The tip may be tapered. The taper may come to a point or may be blunt, such as by having a rounded or flat nose. The self-tapping feature may include one or more recesses in the outer surface of the shaft, such as grooves, extending axially from the first end of the shaft. The grooves may extend axially through a portion of the forward external threads. The grooves may be helically wound along the tip. The grooves may be formed so as to scoop away material, such as bone.

In certain variants, the pitch of the deformable thread of the casing may be different (larger or smaller) from the pitch of an internal thread feature of the bore of the orthopedic implant. In such a scenario, rotating the drive member may cause an axially directed pressure between the deformed thread on the casing and the remainder of the casing.

Other arrangements and combinations within the scope of the appended claims will be apparent upon review of the attached drawings and the following detailed descriptions of the drawings.

BRIEF DESCRIPTION OF THE DRAWINGS

FIG. 1a is a perspective view of an orthopedic locking screw having a casing and configured to be secured through a bore of an orthopedic implant, in accordance with an aspect of the present disclosure;

FIG. 1b is a perspective view of the orthopedic locking screw shown in FIG. 1a, however, without the casing;

FIG. 2a is a perspective view of an orthopedic locking screw having a casing and configured to be secured through a bore of an orthopedic implant, in accordance with another aspect of the present disclosure;

FIG. 2b is a perspective view of the orthopedic locking screw shown in FIG. 2a, however, without the casing;

FIG. 3 is a perspective view of an orthopedic locking screw having projections and a casing in alternate arrangement on the shaft, in accordance with another aspect of the present disclosure;

FIG. 4 is a side view of the orthopedic locking screw shown in FIG. 1a;

FIG. 5 is a perspective partial view of an orthopedic implant having a bore, in accordance with an aspect of the present disclosure;

FIG. 6 is a perspective transverse cross-sectional view of an orthopedic fastening system including an orthopedic locking screw as shown in FIG. 4 secured through a bore of an orthopedic implant as shown in FIG. 5, in accordance with an aspect of the present disclosure;

DETAILED DESCRIPTION

Figure 7:
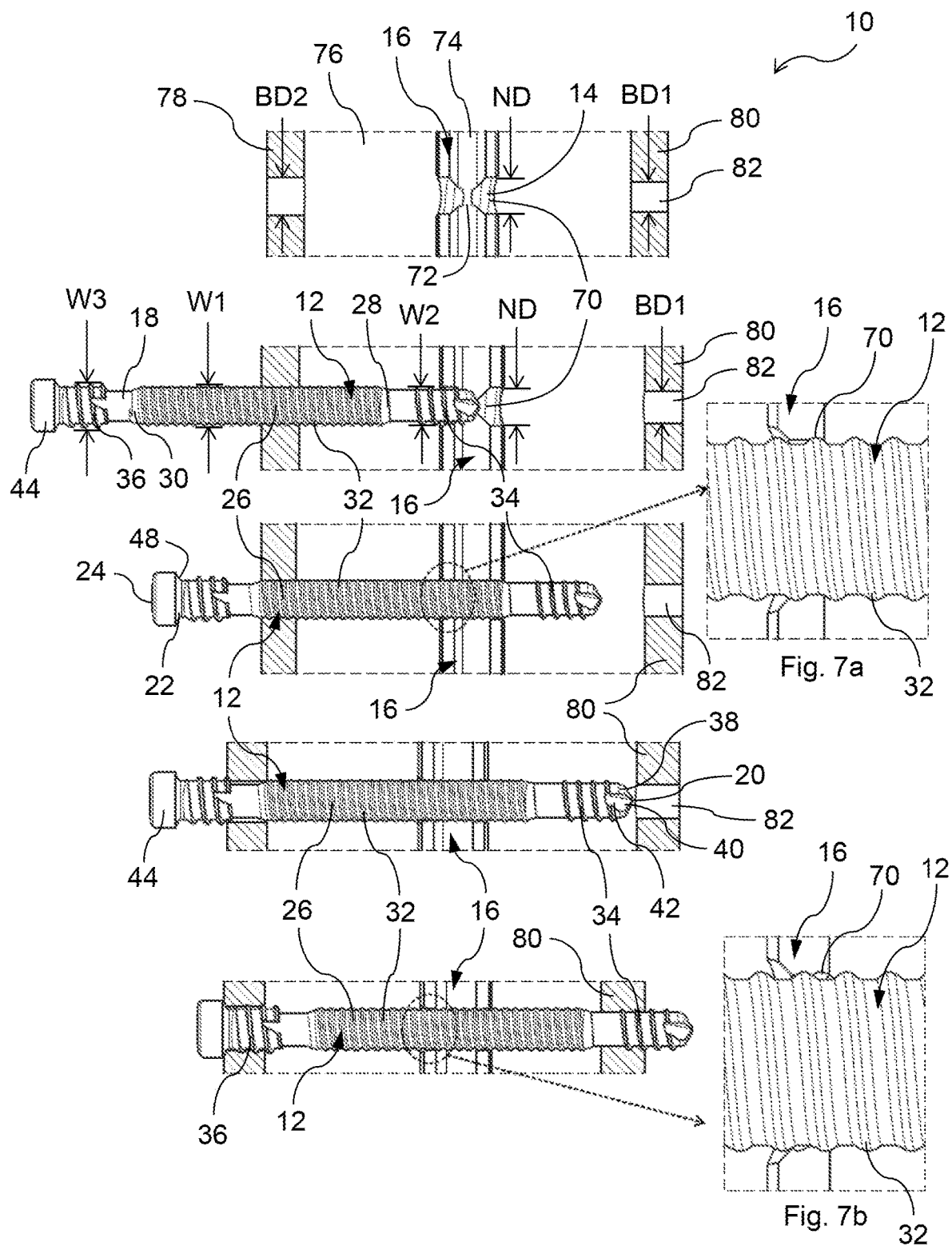
FIG. 7 shows side views of an orthopedic fastening system and a method of securing an orthopedic screw in a bore of an orthopedic implant, in accordance with an aspect of the present disclosure.

Turning now to FIGS. 1a and 1b, an exemplary embodiment of an orthopedic fastening system 10 includes an orthopedic locking screw 12 configured to be operably secured through a bore 14 in an orthopedic implant 16 (not shown), such as a bone nail (e.g., intramedullary nail) or plate, in order to lock the orthopedic implant into a selected position relative to one or more bones or bone portions. The orthopedic locking screw 12 is in certain implementations configured to provide a press-fit, including a friction fit, with the implant to prevent or substantially eliminate movement of the orthopedic implant relative to the orthopedic locking screw 12, such as radially in relation to the axis of the screw and/or angularly, in a selected position relative to the orthopedic implant.

The orthopedic locking screw 12 includes a shaft 18 extending axially between a first end 20 and a second end 22. The shaft 18 may have an elongate, tubular form. The profile of the shaft may be circular or polygonal, such as rectangular, square, or hexagonal. The shaft 18 may be generally cylindrical, having a substantially constant diameter extending between the first and second ends 20, 22. However, in some arrangements, the shaft may have a tubular form with non-circular cross-sections and/or may have varying outside cross-sectional widths. The shaft 18 can have different shapes as long as the orthopedic locking screw 12 is able to operably engage a bore in the implant in such a manner as to be able to retain and, optionally, advance the orthopedic locking screw 12 in and/or through the bore of the orthopedic implant.

A drive member 24 is disposed at the second end 22 of the shaft 18. The drive member 24 may take any form capable of operably engaging with a rotational drive (not shown), such as a screw driver or wrench, so as to be able to rotate the orthopedic locking screw 12 about the axis of the shaft in order to operably engage the orthopedic locking screw 12 with bone and/or the implant. In FIGS. 1a and 1b, the drive member is in the form of a recess, such as a socket, for receiving a rotational member. However, the drive member 24 is not limited to a particular shape or drive arrangement. For example, the drive member 24 may have other shapes, such as having a square or hexagonal circumference for being received in a wrench or a socket, or may have a socket adapted to receive a square or hexagonal drive, or a slot for receiving a screw driver.

A casing 26 is secured as a separate component around an outer surface of the shaft 18. The casing 26 may be secured to the shaft 18 so as to be rotationally fixed with respect to the shaft 18. The casing 26 is formed of a deformable material, such as plastic or a relatively soft metal. The casing may be formed of a rubbery material, such as rubber or silicon. The material forming the casing 26 and/or the shaft 18 may be a bio-compatible material suitable for use as an implant in the human body. The material of the casing 26 is softer than the material of the shaft 18. The material of the shaft 18 can be a plastic, metal or ceramic. The casing 26 is secured to the shaft 18 in a manner configured to prevent one or both of axial slipping and radial slipping along the shaft 18 when operatively engaging the implant (i.e., a bore thereof). For example, the casing 26 may be secured by molding to the shaft 18, adhesive, welding, and/or with mechanical fasteners. The casing 26 may be prevented from circumferential slipping by mechanical interaction with a polygonal shaped profile of the shaft 18.

The casing 26 may have an outer surface that is sized slightly larger than the smallest inside opening space through the implant so as to form a press fit with the implant. The press fit reduces or eliminates radial shifting and movement of the orthopedic implant relative to the axis of the locking screw 12, thereby minimizing the play between the locking screw, the orthopedic implant, and/or bone portions connected thereby. The press fit optionally also may angularly lock the orthopedic locking screw 12 in a selected position in the implant. The casing 26 has an outer cross-sectional width W1 that is larger than a corresponding largest outer cross-sectional width W2 of the shaft 18 between the first end 20 and the second end 22. The press-fit may include axial and/or radial components.

The casing 26 extends axially along a medial portion of the shaft 18. In more detail, the casing 26 extends between a first end 28 and a second end 30. The first end 28 is located proximate the first end 20 of the shaft 18. The second end 30 is disposed proximate the second end 22 of the shaft 18. The casing 26 has a continuous unbroken outer circumferential surface extending between the first and second ends 28 and 30. The first end 28 of the casing 26 is spaced axially from the first 20 of the shaft 18. The second end 30 of the casing 26 is spaced axially from the second end 22 of the shaft 18. The outer surface of the casing 26 may be substantially smooth. Additionally or alternatively, one or more external engagement features 32, such as ribs, tabs, or threads may optionally be formed on the outer surface of the casing 26 configured to operably engage, for example, with internal thread features of a bore of the implant. The engagements features 32 may define a helical path or may not form a helical path, and may take any form arranged to operably engage a thread feature of the implant bore so as to advance and/or retain the casing and the shaft therein. The engagement features 32 may take the form of one or more external threads. In the present embodiment, the engagement features 32 are formed as a deformable thread 32 described elsewhere herein. The deformable thread 32 is disposed along the outer surface of the casing 26.

The deformable thread 32 is an exterior thread having a major diameter Dmaj and a minor diameter Dmin in a manner well understood in the threading art. The shaft 18 and the casing 26 are shown having generally cylindrical shapes with circular cross-sections (as viewed transverse to the axis of the shaft 18). However, it is understood that the shaft 18 and casing 26 are not limited to cylindrical shapes, but may have other tubular and/or non-cylindrical shapes. The use of the terms major and minor diameter are therefore not to be construed as limiting to purely circular cross-sections, but refer rather to the diameter of the circumscribed circle upon, for example, rotating the shaft 18 about its longitudinal axis. The deformable thread 32 may be a continuous thread or it may be a discontinuous thread defined by a plurality of thread portions with intermittent breaks or interruptions therebetween. For example, if the casing 26 has a polygonal cross-section, such as a generally square cross-section, the deformable thread 32 may be defined by intermittent thread portions defined through the outside corners of the cross-section. Of course, other shapes and arrangements are also possible with the same understanding. In the present embodiment, the deformable thread 32 is a continuous thread extending from adjacent the first end 28 of the casing 26 to the second end 30 of the casing 26 as shown in FIG. 1a. The major diameter Dmaj and the minor diameter Dmin of the deformable thread 32 are both constant along the length of the deformable thread 32.

A forward external thread 34 or other type of thread engagement feature, such as ribs, tabs, or grooves, is disposed on the first end 20 of the shaft 18. The forward external thread 34 may be sized to engage a complementary thread feature of an implant bore 14. In the present embodiment, the forward external thread 32 may have a major diameter (i.e., outer diameter) W2 that is smaller than the smallest inside cross-sectional opening through the implant bore 14, such as a minor diameter of internal threads in the bore 14. In other words, the inside diameter of the bore 14 of the orthopedic implant 16 is larger than the outer diameter W2 of the forward external thread 34. The forward external thread 34 operably engages with a bore through bone disposed behind the bore 14 of the implant 16. In this manner, the forward external thread 34 is used to draw the shaft 18 and the casing 26 through the implant bore 14. As the casing 26 advances through the implant bore 14, the outer surface of the casing 26, such as the deformable thread 32, deformably engages with the inner surface or surfaces of the implant bore 14. The deformable engagement creates a press-fit pressure, for example with a friction fit, that stabilizes the orthopedic bone screw 12 angularly and/or axially in a selected position in the implant 16.

In the present embodiment, the forward external thread 34 is disposed on the shaft 18 between the first end 28 of the casing 26 and the first end 20 of the shaft 18. A rear external thread 36 is disposed on the shaft 18 between the second end 30 of the casing 26 and the second end 22 of the shaft 18. In some arrangements, either or both of the external threads 34, 36 may be omitted. The forward external thread 34 is spaced apart axially from the rear external thread 36. The forward external thread 34 is spaced axially from the first end 28 of the casing 26. The rear external thread 36 is spaced axially from the second end 30 of the casing 26. However, in other arrangements, the forward external thread 34 may extend to and/or underneath the first end 28 of the casing 26 and/or the rear external thread 36 may extend to and/or underneath the second end 30 of the casing 26. In yet further arrangements, the forward and rear external threads 34 and 36 may be connected as part of a single thread with a middle portion disposed partially or wholly underneath (i.e., radially inwardly from) the casing 26.

The forward external thread 34 has a major diameter W2 that is smaller than the minor diameter Dmin of the deformable thread 32. In other words, the outer diameter W1 of the deformable thread 32 of the casing 26 is larger than the outer diameter W2 of the forward external thread 34. The rear external thread 36 may have a major diameter W3 equal to or larger or smaller than the forward external thread 34. In the present embodiment, the rear external thread 36 has a major diameter W3 larger than the forward external thread 34 as shown in FIGS. 1a and 1b. The rear external thread 36 is configured to engage a bore through the bone behind the advancement of the sheath 26. In one arrangement, the major diameter W3, W2 of one or both of the rear external thread 36 and the forward external thread 34 is the same as the major diameter Dmaj of the deformable thread 32 along a cylindrical path. In the present embodiment, the outer diameter W3 of the rear external thread 36 is larger than the outer diameter W1 of the deformable thread 32 of the casing 26.

The forward external thread 34 may have a pitch that is different from a pitch of the deformable thread 32 of the casing 28. In the present embodiment, the forward external thread 34 has a pitch that is larger than the pitch of the deformable thread 32 of the casing 28. Alternatively, the pitch of the forward external thread 34 can be smaller than the pitch of the deformable thread 32. The rear external thread 36 has a pitch that is equal to the pitch of the forward external thread 34. Thus, the rear external thread 36 can have a pitch that is smaller or larger than the pitch of the deformable thread 32 of the casing 28.

The deformable thread 32 may have a variable pitch along the length of the casing 26. For example, the deformable thread 32 has a smaller pitch at or near the first end 28 of the casing 26 and increases continuously to a larger pitch at or near the second end 30 of the casing 26. However, other pitch variations capable of causing an axial press-fit pressure with internal threads of the bore 14 of the implant 16 are also possible and contemplated, such as a discontinuous variation of the pitch, a pitch that decreases from the first end 28 toward the second end 30, or other pitch variations. In the present embodiment, the pitch of the deformable thread 32 of the casing 26 is constant along the length of the deformable thread 32.

A pitch difference between the forward external thread 34 and the deformable thread 32 and also a variable pitch of the deformable thread 32 may in certain variants be exploited to reduce or eliminate the amount of shifting and movement between parts of the orthopedic fastening system 10. As an example, in certain variants a press-fit pressure may thus obtained or increased.

As shown in FIGS. 1a and 1b, a tip 38 is disposed at the first end 20 of the shaft 18. The tip 38 tapers to a point or, alternatively, to a blunt nose, such as a rounded, flat, or truncated nose. The tip 38 includes a self-tapping feature 40 for tapping a bore into bone. The self-tapping feature 40 includes at least one, and optionally a pair of diametrically opposite axial grooves 42 extending along the tip 40 through at least a portion of the forward external thread 34 as shown in FIG. 1b. The axial grooves 42 may be at least partially helically wound. The axial grooves 42 may act to scoop away bone or other material as the orthopedic locking screw 12 is rotated and advanced into the bone.

The drive member 24 includes a head 44 disposed at the second end 22 of the shaft 18. The head 44 is configured to engage with a rotational drive member. For example, the head 44 includes a polygonal socket 46 configured to receive a complementary rotary drive (not shown). Other drive configurations may also be used. The head 44 has a larger diameter than the adjacent second end 22 of the shaft 18, thereby forming a shoulder 48 extending radially outwardly from the outer circumferential surface of the second end 22 of the shaft 18 to the outer circumferential surface of the head 44. In other arrangements, the head 44 may be circumferentially smaller than or the same size as the second end 22 of the shaft 18 and/or may include circumferential engagement surfaces, such as having a hex head outer circumferential shape. The head 44 is not limited to the arrangements expressly described, and other arrangements for operably engaging a rotational drive tool may be used.

The casing 26 is secured to the outer surface of the shaft 18 in any manner sufficient to prevent rotational and/or axial sliding of the casing 26 relative to the shaft 18, for example, when the casing 26 is rotationally engaged against an outer or internal surface of the bore 14 of the implant 16. In the present embodiment, the casing 26 is molded directly against the outer surface of the shaft 18 so as to provide a molded securement between the casing 26 and the outer surface of the shaft 18. Alternatively, the casing 26 may be adhesively secured to the outer surface of the shaft 18 with an adhesive. Further, the casing 26 may, alternatively or in addition, be mechanically secured to the outer surface of the shaft 18, for example, by engagement with projections or other surface features with the shaft 18, such as threads, ribs, tabs, grooves, and/or scoring. In the present embodiment as shown in FIGS. 1a and 1b, the shaft 18 has a thread 50 for securing the casing 26 to the shaft 18. FIG. 1b illustrates the orthopedic locking screw 12 without the casing 26. The thread 50 of the shaft is substantially equal to the deformable thread 32 of the casing. Further the thread 50 may have substantially equal dimensions and/or pitch as the deformable thread 32 of the casing. The casing 26 directly engages the thread 50 of the shaft 18, e.g., is directly molded against the thread 50 of the shaft 18. By molding or adhering the casing 26 to the shaft 18, the thread 50 may act as a preform to form the basic structure of the deformable thread 32.

Turning now to FIGS. 2a and 2b, another embodiment of an orthopedic locking screw 52 is shown. The orthopedic locking screw 52 is similar to the orthopedic locking screw 12 in that it includes a shaft 18 extending between first and second ends 20 and 22, a drive member 24 disposed at the second end 22, and a casing 26 secured around an outer surface of the shaft 18, wherein the casing 26 includes a deformable thread 32 and the shaft 18 includes a forward and rear external thread 34, 36. A description thereof is not repeated here for brevity, but reference is made to the previous description in view of the following additional or alternative arrangements.

One difference between orthopedic locking screw 52 and orthopedic locking screw 12 is that the shaft 18 of orthopedic locking screw 52 includes at least one groove 54. FIG. 2b illustrates the orthopedic locking screw 52 without the casing 26. In the present embodiment as show in FIG. 2b, the shaft 18 of orthopedic locking screw 52 has four grooves 54. Alternatively, the shaft 18 of orthopedic locking screw 52 may include one, two, three or more grooves 54.

The groove 54 extends circumferentially around and axially along the outer surface of the shaft 18. The casing 26 is disposed in the groove 52 such that the groove 52 helps secure the casing 26 on the outer surface of the shaft 18. The groove 54 may have a continuous polygonal core profile, such as a rectangle, square, or hexagon, a continuous arcuate profile, such as circular or oval, or both polygonal and arcuate profiles. The shaft 18 comprises a polygonal or other non-circular profile in cross-section (i.e., cross-sectional shape transverse to the longitudinal axis of the shaft) that prevents the casing 26 from rotationally slipping on the shaft 18. In the exemplary arrangement of FIG. 2b, the grooves 52 have a circular core profile 56. The circular core profile 56 extends continuously along the entire axial length of the groove 54. In some arrangements, the groove 54 and/or other portions of the shaft 18 may have other core profile shapes, such as star or gear tooth shape formed by elongate ribs or other shaped protrusions or recesses.

The groove 54 has a smaller outside diameter than the adjacent portions of the shaft 18. The grooves 54 in this arrangement are spaced around the outer circumference of the shaft 18. Alternatively, one groove may extend radially completely around the outer circumference of the shaft 18. As shown in FIG. 2b, the grooves 54 extend axially from a first radial shoulder 58 proximate the first end 20 of the shaft 18 to a second radial shoulder 60 proximate the second end 22 of the shaft 18. The entire axial length of the casing 26 is received within the grooves 54. The first end 28 of the casing 26 abuts the first radial shoulder 58. The second end 30 of the casing 26 abuts the second radial shoulder 60. Thus, the radial shoulders 58 and 60 mechanically retain the casing 26 axially fixed along the length of the shaft 18. The casing 26 has a thickness that is larger than the radial dimension of the groove 54 such that the outer circumferential surfaces of the casing 26 project radially beyond the outer circumferential surfaces of the adjacent first and second ends 20 and 22 of the shaft 18, in accordance with the previous description. A radially inner surface of the casing 26 may additionally or alternatively be secured against the radially outer surface of each groove 54 by other fastening connections, such as an adhesive, or an over molded connection, welds, or mechanical fastening features.

FIG. 3 illustrates another embodiment of an orthopedic locking screw 62. The orthopedic locking screw 62 is similar to the orthopedic locking screw 12 in that it includes a shaft 18 extending between first and second ends 20 and 22, a drive member 24 disposed at the second end 22, and a casing 26 secured around an outer surface of the shaft 18, wherein the casing 26 includes a deformable thread 32 and the shaft 18 includes a forward and rear external thread 34, 36. The descriptions thereof are not repeated here for brevity, but reference is made to the previous description in view of the following additional or alternative arrangements.

One difference between orthopedic locking screw 12 of FIGS. 1a and 1b and the orthopedic locking screw 62 shown in FIG. 3 is that shaft 18 includes projections 64. The projections 64 are disposed on the outer surface of the shaft 18. The projections 64 may be arranged on the shaft 18 along a helical curve around the shaft 18, e.g., in similar fashion as a thread or thread sections. The projections 64 may be produced by forming or cutting a thread on the shaft 18 and then, milling of portions of the thread, thus forming gaps within the thread.

The casing 26 is secured to and rotationally fixed around the outer surface of the shaft 18, wherein the casing 26 is formed around the projections 64. In the present embodiment, the projections 64 and deformable protrusions of the casing 28 are alternately arranged on the outer surface of the shaft 18. The projections 28 and the casing 26 together form a thread-like feature along the shaft 18 as shown in FIG. 3. In the present embodiment, a partially deformable thread 66 is thus formed by the protrusions of casing 26 and the projections 64 of shaft 18. In addition, shaft 18 of orthopedic locking screw 62 may have one or more of grooves 54 as described above and as shown in FIGS. 2a and 2b. In such an embodiment, the projections 64 can be arranged along the shaft 18 between the grooves 54.

Turning now to FIGS. 4 to 6, the orthopedic fastening system 10 is shown. The orthopedic fastening system 10 includes orthopedic locking screw 12 as shown in FIGS. 4 and 6 and an exemplary orthopedic implant 14 as shown in FIGS. 5 and 6. Orthopedic locking screw 52 or 62 as described above could also be used in combination with the orthopedic implants of any of the drawings shown herein as part of this orthopedic fastening system. The orthopedic implant 14 may have any of various specific forms.

FIG. 4 illustrates orthopedic locking screw 12 in a side view. As described above with reference to FIGS. 1a and 1b, orthopedic locking screw 12 includes the shaft 18 extending between first and second ends 20 and 22, the drive member 24 disposed at the second end 22, and the casing 26 secured around an outer surface of the shaft 18, wherein the casing 26 includes the deformable thread 32 and the shaft 18 includes the forward and rear external thread 34, 36. A description thereof is not repeated here for brevity, but reference is made to the previous description in view of the following additional or alternative arrangements.

The first end 28 of the casing 26 is tapered radially inwardly, as at 68, toward the outer diameter of the front end 20 of the shaft 18 immediately adjacent the first end 28 of the casing 26. In this arrangement, the deformable thread 32 runs out at a location along the taper 68 before reaching the first end 28, such that the deformable thread 32 has a first end spaced along the taper 68 adjacent to and spaced from the first end 28 of the casing 26. Alternatively, the thread 32 may run entirely to the first end 28 of the casing 26. In some arrangements, the taper 68 is such that there is a smooth transition between the first end 28 of the casing 26 and the shaft 18. In other arrangements, the first end 28 of the casing 26 may have a larger diameter than the adjacent portion of the shaft 18 so as to form a radially stepped transition. The remaining portion of the outermost diameter of the casing 26 may be substantially cylindrical from the taper 68 to the second end 30 or may have a different taper or other width variations. Alternatively, the outermost diameter of the casing 26 may be substantially cylindrical along the entire axial length between the first end 28 and the second end 30.

In one exemplary embodiment, the orthopedic locking screw 12 preferably has an overall length of between 125 mm and 5 mm, and more preferably between approximately 70 mm and 50 mm. The casing 26 preferably has a length of between 100 mm and 3 mm and more preferably between approximately 40 mm and 30 mm. The casing 26 preferably has an outside diameter of between 52 mm and 0.9 mm, more preferably between 12 mm and 5 mm, and most preferably between approximately 6 mm and 4 mm, and in some arrangements approximately 5.2 mm or 5.3 mm. In one arrangement, the deformable thread 32 preferably has a major diameter of between 51 mm and 0.8 mm, more preferably between 11 mm and 4 mm, and most preferably between approximately 6 mm and 4 mm, and in some arrangements approximately 5.3 mm or 5.5 mm, a minor diameter of between 50 mm and 0.7 mm, more preferably between 10 mm and 2 mm, and in some arrangements approximately 4.3 mm or 4.5 mm. In a further arrangement, the deformable thread 32 may have a variable pitch that varies continuously along the axial length of the casing from between approximately 0.5 to 2 threads/mm adjacent the first end 28 to between approximately 0.1 to 1 threads/mm at the second end 30. Preferably, the deformable thread 32 may have a constant thread pitch along the axial length of the casing between 0.5 to 2 threads/mm, more preferably between 0.9 and 1.5 threads/mm, and in some arrangements approximately 1.25 threads/mm or 1.3 threads/mm. The shaft 18 may have an average diameter of between 50 mm and 0.7 mm, more preferably between 20 mm and 3 mm, and in some arrangements between approximately 4.9 mm and 5.1 mm. Either or both of the forward external thread 34 and the rear external thread 36 may have a major diameter of between 52 mm and 0.9 mm, more preferably between 12 mm and 4 mm, and most preferably between approximately 7 mm and 5 mm, and in some arrangements approximately 5 mm or 6 mm. Further, either or both of the forward external thread 34 and the rear external thread 36 may have a constant thread pitch along the axial length thereof between 0.5 to 2 threads/mm, more preferably between 1.0 and 1.9 threads/mm, and most preferably between approximately 1.7 and 1.8 threads/mm and in some arrangements approximately 1.75 threads/mm. However, the specific dimensions provided herein are only exemplary of one optional exemplary arrangement, and the invention is not limited to the specific dimensions provided.

FIG. 5 shows a perspective partial view of the orthopedic implant 16 having a bore 14. The orthopedic implant 16 may be formed of a biocompatible material suitable and/or approved for use as an implant inside a human body. In some arrangements, the orthopedic implant 16 is formed of metal, plastic, and/or ceramic. The orthopedic implant 16 may be any type of orthopedic implant. Some exemplary types of orthopedic implants include plates and bone nails like intramedullary nails.

The bore 14 of the orthopedic implant 16 may be smooth and/or include an internal surface feature, such as an internal thread, having a radially internal arrangement suitable for operably engaging external threads or any other engagement structures on the locking screw 12, for example configured to retain and, optionally, advance any of the orthopedic locking screws disclosed herein upon rotating the locking screw inside the bore 14. Thus, for example, the bore 14 may in some embodiments be formed of a thin bore that does not have helical threads but has edges that interact with external helical threads or thread-like features to advance and/or retain an orthopedic locking screw. In other embodiments, the bore 14 may include one or more radially internally projecting protrusions that are similarly able to operably interact with external helical threads or thread engagement features. In yet further embodiments, the bore 14 may include one or more helical internal threads, either alone, or in combination with other thread-like features.

In the present embodiment as shown in FIG. 5, the orthopedic implant 16 includes one exemplary bore 14, although the orthopedic implant 16 may include any number of such bores 14. The bore 14 is a through bore extending transversely through the orthopedic implant 16 from a first side to a second side. The bore 14 is internally threaded, including an internal thread 70 helically wound along an inner circumferential surface of the bore 14. Further, the bore 14 includes a circumferential rib 72 extending around and projecting radially inwardly from the inner circumferential surface of the bore 14. The circumferential rib 72 is spaced medially through the bore 14, such as being spaced half way between the first and second sides of the bore 14. The internal thread 70 traverses the inner circumferential surface of the circumferential rib 72. Further, the orthopedic implant 16 includes a channel 74 in the direction of its longitudinal axis. The channel 74 crosses the threaded bore 14, i.e., the channel opens out into bore 14 as shown in FIG. 5.

FIG. 6 illustrates orthopedic locking screw 12 of FIG. 4 inserted into the bore 14 of orthopedic implant 16 of FIG. 5 as a perspective transverse cross-sectional partial view.

In the present arrangement, the forward external thread 34 is sized so as to not operably engage the bore 14 of the orthopedic implant 16 but is configured mainly for engaging with bone on either or both sides of the bore 14 (not shown in FIG. 6). For example, the major diameter of the forward external thread 34 is smaller than the minor diameter of the internal thread 70 so that the forward external thread 34 does not operably engage the internal thread 70 but can be pushed through the bore 14 without interference. In other arrangements, however, the forward external thread 34 may be sized to operably engage the bore 14. For example, the major diameter of the forward external thread 34 may be larger than a minimum opening width through the bore 14.

The deformable thread 32 is configured to engage with the bore 14 so as to operably retain the shaft 18 in the bore 14 with a press-fit and/or mechanical interfit. As shown in FIG. 6, the deformable thread 32 is configured to engage with one or more interior thread features, such as one or more interior threads 70, in the bore 14 in a manner configured to cause at least one or both of a radial press-fit pressure and an axial press-fit pressure. The deformable thread 36 optionally is configured to at least partially receive the inner circumference of the circumferential rib 72 within the groove of the thread. However, it is not necessary for the deformable thread 32 to perfectly match the configuration of the internal thread 70 because it can deform to adjust to the internal thread 70. In present arrangement, the internal threads 70 axially engage and increasingly deform the axial walls of the deformable thread 32 as the thread 32 is advanced through the bore 14, thereby giving rise to a variable, and in this case, increasing, axial press-fit pressure as the orthopedic locking screw 12 is advanced through the bore 14. The insertion and locking process of the orthopedic locking screw 12 will be described with reference to FIGS. 7 and 8 below in more detail.

The press-fit is configured to prevent or substantially eliminate movement of the orthopedic implant 16 relative to the orthopedic locking screw 12, such as radially in relation to the shaft 18 and/or angularly, in a selected position relative to the orthopedic implant 16. Thus, the press fit reduces or eliminates radial shifting and movement of the orthopedic implant 16 relative to the axis of the locking screw 12, thereby minimizing the play between the locking screw, the orthopedic implant, and/or bone portions connected thereby. The press fit optionally also may angularly lock the orthopedic locking screw 12 in a selected position in the bore 14. Thus, the orthopedic locking screw 12 can be secured through the orthopedic implant 16.

The pitch of the deformable thread 32 of the casing 26 is, in the present arrangement, substantially equal to the pitch of the internal thread 70 of the bore 14 of the orthopedic implant 16. In this case an axial press-fit pressure is caused when the forward external thread 34 comes into contact with the bone on the opposite side of the orthopedic implant 16 by drawing the shaft 18 and the casing 26 through the implant bore 14. Alternatively, the pitch of the deformable thread 32 of the casing 26 can be slightly different from the pitch of the internal thread 70 of the bore 14 of the orthopedic implant 16, thereby achieving, alternately or in addition, an axial press-fit pressure during screwing in of the orthopedic locking screw 12 into implant bore 14. In this case, the pitch of the deformable thread 32 of the casing 26 may also be larger or smaller than the pitch of the internal thread 70 of the bore 14 of the orthopedic implant 16.

In the present embodiment, the diameter of the deformable thread 32 of the casing 26 is substantially equal to the diameter of the internal thread 70 of the bore 14 of the orthopedic implant 16. The minor diameter Dmin of the deformable thread 32 is constant along the length of the thread. However, in other arrangements, the minor diameter Dmin may vary along the length, such as by increasing continuously or discontinuously from the first end 28 toward the second end 30. In the arrangement of FIG. 6, the deformable thread 32 is sized such that the minor diameter Dmin is substantially equal to the minor diameter of the internal thread 70. In order to optionally achieve a radial press-fit pressure, at least one outside cross-sectional width of the casing 26, such as either the major diameter Dmaj or the minor diameter Dmin, may be sized to be larger than a corresponding smallest inside cross-sectional opening of the bore 14, such as the corresponding minor diameter or the major diameter of the internal thread 70. Thus, the major diameter Dmaj of the deformable thread 32 may be larger than the major diameter of the internal thread 70. Additionally or alternatively, the minor diameter Dmin of the deformable thread 32 may be larger than the minor diameter of the internal thread 70 to create a radial press-fit pressure. However, other embodiments may include only one or the other feature or both features so as to form only a radial press-fit pressure or an axial press-fit pressure or both press-fit pressures if desired.

Figure 8:
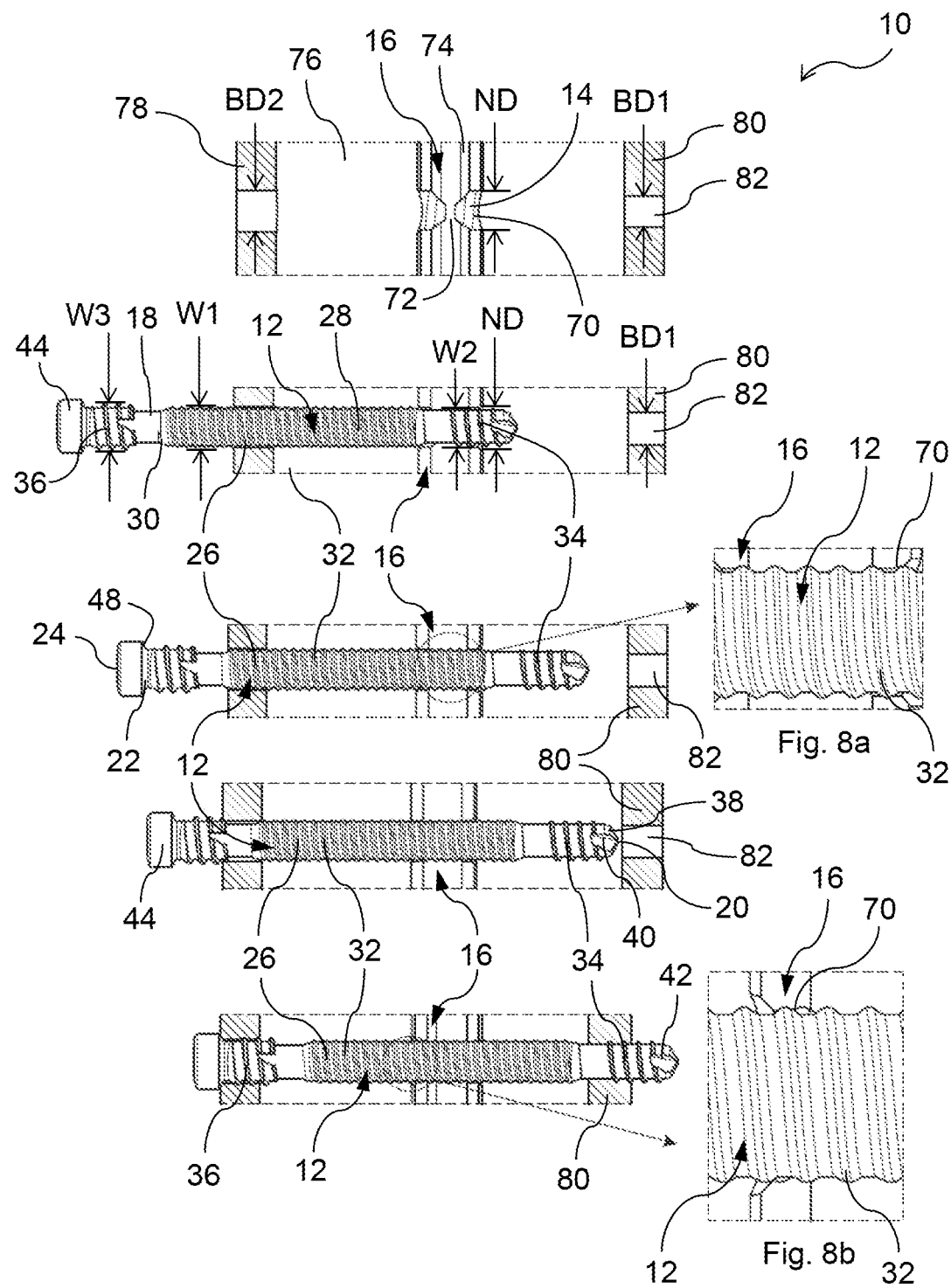
FIG. 8 shows side views of an orthopedic fastening system and a method of securing an orthopedic screw in a bore of an orthopedic implant, in accordance with another aspect of the present disclosure.

Turning now to FIGS. 7 and 8, both drawings show side views of an orthopedic fastening system embodiment and a method of securing an orthopedic screw 12 in a bore 14 of an orthopedic implant 16 (in the form of an intramedullary nail). As shown, the orthopedic locking screw 12 will operably be engaged with, such as in and/or through, the bore 14.

The intramedullary nail 16 includes at least one, and optionally several bores 14. The bores 14 may be threaded bores and/or include any and/or all of the features of the bore 14 previously described herein. The orthopedic locking screw 12 is the same as described previously. The descriptions thereof are not repeated here for brevity, but reference is made to the previous explanations in view of the following additional or alternative arrangements. Remaining aspects of this system are substantially similar as corresponding portions previously described herein and are not repeated here for the sake of brevity. Alternatively or in addition, other orthopedic locking screw embodiments as described above or hereinafter could be used with the orthopedic systems shown in FIG. 7 or 8.

The methods described herein are not limited to the orthopedic locking screw 12 and the orthopedic implant 16. Rather, the methods may be used to engage any one of the orthopedic screws to any one of the bores disposed in any one of the orthopedic implants and/or the intramedullary nail disclosed herein or otherwise.

With reference to FIG. 7, a first method of securing an orthopedic locking screw to a bore will be described. Thus, the following description, while focused mainly on the arrangement shown in FIG. 7 for exemplary reasons, also refers to other arrangements. It is to be understood that this method is not limited to the exact description of these particular arrangements, but can be applied to any arrangement in a manner that would be understood by the ordinarily skilled person.

In the case according to FIG. 7, the forward external thread 34 of orthopedic locking screw 12 has a pitch that is different (e.g., larger) from the pitch of the deformable thread 32 of the casing 26. For example, the pitch of the forward external thread 34 is about 1.75 and the pitch of the deformable thread 32 is about 1.25. Generally, the pitch difference could range between 0.1 and 1.0. Further, the pitch of the deformable thread 32 is substantially equal to the pitch of the internal thread 70 of the implant bore 14, but it could also be different.

The intramedullary nail 16 is inserted in bone 80 comprising marrow 76. The marrow 76 is circumferentially encased by cortex as illustrated by a first cortex portion 78 (on the left in FIGS. 7 and 8) and a second cortex portion 80 (on the right in FIGS. 7 and 8).

In a further step, the first end 20 of the shaft 18 is inserted through the first cortex portion 78 and marrow 76 into the bore 14 of the orthopedic implant 16.

The shaft 18 is advanced into the bore 14 in any sufficient manner, such that the forward external thread 34 is advanced through the bore 14, for example by driving. When the deformable thread 32 of the casing 26 comes into engagement the internal thread 70 of the bore 14, the shaft 18 may be rotated, for example with a rotational drive tool engaged with the drive member 24, to advance the shaft 18 and the casing 26 into and/or through the bore 14. In this case, the deformable thread 32 operably (threadably) engages the bore 14 so as to form a mechanical interfit with the internal thread 70 of the bore 14 as shown in FIG. 7*a*.

The shaft 18 is advanced through the bore 14 in any manner, as appropriate. When the forward external thread 34 comes into engagement with bone on the opposite side of the orthopedic implant 16, i.e., with the second cortex portion 80, the drive member 24 is rotated further, which rotates the shaft 18 and the casing 26, so as to operably (threadably) engage the forward external thread 34 with bone. Due to the fact that the pitch of the forward external thread 34 is different (e.g., larger) from the pitch of the deformable thread 32, the forward external thread 34 operates to advance (e.g., by pulling) the shaft 18 and the casing 26 forward through the bore 14 of the orthopedic implant 16. Thereby, the bore 14 and, specifically, its internal thread 70 deforms the casing 26 and its deformable thread 32, respectively, axially and/or radially. The deformation of the deformable thread 32 results in a press-fit of the casing 26 against the bore 14 in an axial pressure direction and/or a radial pressure direction as shown in FIG. 7*b*.

The press-fit pressure may increase as the casing 26 advances through the bore 14. For example, where the deformable thread 32 has a variable pitch, increased axial press-fit pressure may be developed as the casing 26 advances through the bore 14. Where the deformable thread has an increasing outside diameter, such as an increasing minor diameter and/or major diameter, increased radial press-fit pressure may be developed as the casing 26 advances through the bore 14. The outer surface of the casing 26 could also be cylindrical and any deformable thread 32 could have a constant pitch along the length of the casing, in which case the press-fit pressure may remain substantially constant as the casing 26 advances through the bore 14. Additionally, the rear external thread 36 may also operate to advance (e.g., by pushing) the shaft 18 and the casing 26 through the bore 14 by engaging with the bone on the insertion side of the orthopedic implant 16, i.e., with the first cortex portion 78.

Now turning to FIG. 8, the drawing shows another orthopedic locking system embodiment and a second method of securing an orthopedic locking screw 12 to a bore 14 of an orthopedic implant 16. The difference between the orthopedic locking system and method of FIG. 8 and that described with reference to FIG. 7 is that the pitch of the deformable thread 32 of orthopedic locking screw 12 is different (e.g., slightly larger) from the pitch of the internal thread 70 of the implant bore 14. For example, the pitch of the deformable thread 32 is about 1.3 and the pitch of internal thread 70 of the implant bore 14 is about 1.25. Generally, the pitch difference could range between 0.01 and 0.3. The forward external thread 34 of orthopedic locking screw 12 can still have a pitch that is different (e.g., larger) from the pitch of the deformable thread 32 of the casing 26. Remaining aspects of the system and method are substantially similar as previously described herein and is not repeated here for the sake of brevity.

In the particular system and method according to FIG. 8, the pitch of the deformable thread 32 is slightly larger than the pitch of the internal thread 70 of the implant bore 14. Thus, in the step where the shaft 18 is rotated, for example with a rotational drive tool engaged with the drive member 24, to advance the shaft 18 and the casing 26 into and/or through the bore 14 and the deformable thread 32 operably engages the internal thread 70 of the bore 14, an axial press-fit pressure is achieved due to the different thread pitches of the deformable thread 32 and the internal thread 70. In this case, the deformable thread 32 and/or the internal thread 70 itself operates to advance (e.g., by pulling) the shaft 18 and the casing 26 forward through the bore 14 of the orthopedic implant 16 during screwing in of the orthopedic locking screw 12 into implant bore 14. Thereby, the bore 14 and its internal thread 70 (slightly) deforms the casing 26 and its deformable thread 32, respectively, axially, thereby developing an axial press-fit of the casing 26 against the bore 14 in an axial pressure direction as shown in FIG. 8*a*.

Once the forward external thread 34 comes into engagement with bone on the opposite side of the orthopedic implant 16, i.e., with the second cortex portion 80, the drive member 24 is rotated further, which rotates the shaft 18 and the casing 26, so as to operably (threadably) engage the forward external thread 34 with bone. If the pitch of the forward external thread 34 is also different (e.g., larger) from the pitch of the deformable thread 32, the forward external thread 34 operates to advance (e.g., by pulling) the shaft 18 and the casing 26 forward through the bore 14 of the orthopedic implant 16. Thereby, the bore 14 and its internal thread 70 further deforms the casing 26 and its deformable thread 32, respectively, axially and/or radially, thereby increasing the press-fit of the casing 26 against the bore 14 in an axial pressure direction and/or a radial pressure direction as shown in FIG. 8*b*.

An aspect of the second system and method as described with reference to FIG. 8 is that once the forward external thread 34 engages the bone 80 and is operated to draw the shaft 18 and the casing 26 forward through the implant bore 14, the deformable thread 32 cannot engage with the internal thread 70 of the implant bore 14 again.

Next, a further method embodiment of securing an orthopedic screw 12 in a bore 14 of an orthopedic implant 16 is described with reference to FIGS. 7 and 8. This embodiment can be combined with the method embodiments described above.

In a first step, a bore 82 having a first diameter BD1 is drilled into bone, e.g., into the first and second cortex portions 78, 80. BD1 may range between 3 mm and 6 mm (e.g., between 3.5 mm and 5 mm, such as 4.2 mm). Then, at least a part of the bore 82 (e.g., the bore portion in the first cortex portion 78) is widened by drilling with a second diameter BD2. BD may range between 4 mm and 7 mm (e.g., between 4.5 mm and 6 mm, such as 5.3 mm). The orthopedic implant 16 can be inserted in the marrow cavity 76 of bone before or after the above bone drilling steps. If the intramedullary nail 16 is inserted before drilling the first bore through bone, the drilling operation may be performed through the implant bore 14 of the intramedullary nail 16.

Then an orthopedic locking screw 12 as generally described above or hereinafter is provided. As explained above, the orthopedic locking screw 12 includes the shaft 18 extending axially between the first end 20 and the second end 22, the drive member 24 disposed at the second end 22, and the casing 26 secured to and rotationally fixed around the outer surface of the shaft 18, wherein the casing 26 is formed of a (e.g., plastically) deformable material. The casing 26 has an outer cross-sectional width W1 that is larger than a smallest inside cross-sectional width ND of the bore 14 of the orthopedic implant 16. The first end 20 of the shaft 18 has an outer cross-sectional width W2 that is smaller than the smallest inside cross-sectional width ND of the bore 14 of the orthopedic implant 16 but larger than the first diameter BD1 of the bore 82 in the bone 80. The system and locking screw may have further aspects substantially corresponding to portions previously described herein and is not repeated here for the sake of brevity.

The first end 20 of the shaft 18 is inserted into the bore 14 of the orthopedic implant 18. Then, the casing 26 comes into engagement with the bore 14 of the orthopedic implant 18.

By rotating the drive member 24, the shaft 18 and the casing 24 are rotated so as to operably (e.g., threadably) engage the casing 26 with the bore 14 of the orthopedic implant 16, thereby achieving an advance of the orthopedic locking screw 12 through the bore 14 of the orthopedic implant 16.

When the first end 20 of the shaft 18 comes into engagement with the bore 82 having the first diameter BD1 in the bone 80 on the opposite side of the orthopedic implant 16, the drive member 24 is rotated further to rotate the shaft 18 and the casing 26 so as to operably (e.g., threadably) engage the first end 20 of the shaft 18 with bone 80, thereby advancing, e.g., pulling, the shaft 18 and the casing 24 through the bore 14 of the orthopedic implant 16 and achieving a deformable press-fit of the casing 26 against the bore 14 of the orthopedic implant 16.

Specifically, upon the operable engagement of the forward external thread 34 with the second cortex portion 82, the different thread pitches result in a deformation of the deformable thread 32 of the casing 26 against the orthopedic implant 16 as the shaft 18 and the casing 26 are pulled through the bore 14, thereby achieving the deformation of the deformable thread 32 of the casing 26 against the orthopedic implant 16.

An aspect of the third method embodiment as described above with reference to FIGS. 7 and 8 is the fact that the second diameter BD2 of the "input" side opening of the cortex exceeds the first diameter BD1 of the "output" side opening of the cortex. The increased second diameter BD2 permits an easier advance of the casing 26 through the cortex. Specifically, damaging of the "input" side cortex and/or the casing 26 upon the shaft 18 being moved through the "input" side opening of the cortex can be reduced or even prevented. At the same time the forward external thread 34 can operably engage the "output" side opening.

The above described methods and steps thereof can be individual combined with each other or extended with further steps or procedures as desired. In similar manner, the methods described can provide different locking screw embodiments and/or orthopedic implant embodiments as desired.

When the orthopedic locking screw 12 is disposed in a selected position, the press-fit pressure between the casing 26 and the internal surface of the bore 14 prevents or reduces undesired rotational movement and/or lateral movement and/or axial movement of the orthopedic locking screw 12 relative to the bore 14, and optionally also to the orthopedic implant 16.

The orthopedic locking screws of the present disclosure provide in some circumstances a tighter fit with the bore of, for example, an orthopedic implant, such as an intramedullary nail or a plate, or a bone, than has been heretofore achievable with a single orthopedic screw. As a result, undesired movement and shifting between the connected bone portions and/or the orthopedic implant may be reduced, thereby improving the healing process of the bone. In addition, the improved locking capability of the orthopedic locking screws may allow the number of locking elements needed in an orthopedic fastening system to be decreased. Other technical advantages and/or usefulness are also possible.

The features described in relation to the exemplary arrangements shown in the drawings can be readily combined to result in different embodiments, as suggested previously above. It is apparent, therefore, that the present disclosure may be varied in many ways. Such variations are not to be regarded as a departure from the scope of the invention, and all modifications within the scope of the appended claims are intended to be expressly included therein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic locking screw configured to be secured through a bore, provided with an engagement feature, of an orthopedic implant, the orthopedic locking screw comprising:
    a shaft extending along an axis between a first end and a second end;
    a casing having a first end proximate the first end of the shaft and a second end proximate the second end of the shaft, the casing secured to an outer surface of the shaft such that during securing of the orthopedic locking screw through the bore of the orthopedic implant the casing is rotationally and axially fixed around the outer surface of the shaft and prevented from slipping radially relative thereto;
    a deformable thread disposed along an outer surface of the casing configured to deform when the deformable thread engages the engagement feature as the orthopedic locking screw is secured through the bore of the orthopedic implant; and
    a forward external thread disposed on the shaft between the first end of the casing and the first end of the shaft, wherein the forward external thread has a pitch that is different from a pitch of the deformable thread of the casing.

2. The orthopedic locking screw of claim 1, wherein the forward external thread has a pitch that is larger than the pitch of the deformable thread of the casing.

3. The orthopedic locking screw of claim 1, wherein the deformable thread is an external thread and the engagement feature of the bore is an internal thread so as to retain the shaft in the bore.

4. The orthopedic locking screw of claim 1, wherein the deformable thread is a continuous thread extending from adjacent the first end of the casing to the second end of the casing.

5. The orthopedic locking screw of claim 1, wherein the deformable thread has a minor diameter and a major diameter, wherein at least one of the minor and major diameters is constant along the length of the deformable thread.

6. The orthopedic locking screw of claim 5, wherein the outer diameter of the deformable thread of the casing is larger than an outer diameter of the forward external thread.

7. The orthopedic locking screw of claim 1, wherein the casing is integrally formed with the deformable thread and wherein at least one of the casing and the deformable thread is formed of a plastically deformable material.

8. The orthopedic locking screw of claim 1, further comprising a rear external thread disposed on the shaft between the second end of the shaft and the second end of the casing.

9. The orthopedic locking screw of claim 8, wherein the rear external thread has a pitch that is equal to the pitch of the forward external thread.

10. The orthopedic locking screw of claim 8, wherein at least one of the forward external thread and the rear external thread is axially spaced apart from the casing.

11. The orthopedic locking screw of claim 8, wherein an outer diameter of the rear external thread is larger than the outer diameter of the deformable thread of the casing and wherein the outer diameter of the rear external thread is equal to or larger than the outer diameter of the forward external thread.

12. The orthopedic locking screw of claim 1, wherein the casing has an outer cross-sectional width that is larger than a cross-sectional width of the first end of the shaft adjacent the first end of the casing.

13. The orthopedic locking screw of claim 1, wherein the first end of the casing is tapered radially inwardly toward the outer surface of the shaft.

14. The orthopedic locking screw of claim 1, wherein the shaft comprises a polygonal or other non-circular profile that prevents the casing from rotationally slipping on the shaft.

15. The orthopedic locking screw of claim 1, further comprising a tip disposed at the first end of the shaft, wherein the tip comprises a self-tapping feature.

16. The orthopedic locking screw of claim 1, further comprising a drive member disposed at the second end of the shaft, the drive member comprising a head configured to engage with a rotational drive member, wherein the head forms a shoulder extending radially outwardly from an outer surface of the shaft to an outer surface of the head.

17. The orthopedic locking screw of claim 1, wherein a material of the casing is softer than a material of the shaft, the material of the casing preferably comprising at least one of a plastic and a metal, and the material of the shaft preferably comprising at least one of a plastic, a metal, and a ceramic.

18. The orthopedic locking screw of claim 1, wherein the orthopedic locking screw is configured to be secured through an orthopedic implant formed of a biocompatible material and comprising the bore.

19. An orthopedic fastening system, comprising:
an orthopedic implant comprising a threaded bore; and
an orthopedic locking screw configured to be restrained inside the threaded bore, the orthopedic locking screw comprising:
a shaft extending along an axis between a first end and a second end, the first end sized to be received in the threaded bore;
a casing having a first end proximate the first end of the shaft and a second end proximate the second end of the shaft, the casing secured to an outer surface of the shaft such that during securing the orthopedic locking screw through the threaded bore of the orthopedic implant the casing is rotationally and axially fixed around the outer surface of the shaft and prevented from slipping radially relative thereto;
a deformable thread disposed along an outer surface of the casing, wherein the deformable thread is configured to deform when engaged with a complementary internal thread feature of the threaded bore as the orthopedic locking screw is screwed through the threaded bore of the orthopedic implant; and
a forward external thread disposed on the shaft between the first end of the casing and the first end of the shaft, wherein the forward external thread has a pitch that is different from a pitch of the deformable thread of the casing.

20. An orthopedic locking screw configured to be secured through a bore, provided with an engagement feature, of an orthopedic implant, the orthopedic locking screw comprising:
a shaft having projections disposed on an outer surface of the shaft; and
a casing secured to the outer surface of the shaft such that during securing the orthopedic locking screw through the bore of the orthopedic implant the casing is rotationally and axially fixed around the outer surface of the shaft and prevented from slipping radially relative thereto, wherein the casing is formed of a deformable material configured to deform when engaged with the engagement feature as the orthopedic locking screw is secured through the bore of the orthopedic implant,
wherein the projections and the casing are alternately arranged on the outer surface of the shaft, such that the projections and the casing together form a thread-like feature along the shaft.

* * * * *